US00PP21288P2

(12) United States Plant Patent
Verhoef

(10) Patent No.: US PP21,288 P2
(45) Date of Patent: Sep. 14, 2010

(54) ***WEIGELA* PLANT NAMED 'VERWEIG 4'**

(50) Latin Name: *Weigela florida*
Varietal Denomination: Verweig 4

(76) Inventor: Gijsbertus Verhoef, Burgemeester Smitweg 37, Hazerswoude (NL)

( * ) Notice: Subject to any disclaimer, the term of this patent is extended or adjusted under 35 U.S.C. 154(b) by 0 days.

(21) Appl. No.: 12/456,302

(22) Filed: Jun. 15, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Jondle & Associates, P.C.

(57) ABSTRACT

'Verweig 4' is a new *Weigela* plant particularly distinguished by purple flowers, a moderately vigorous growth habit and green, pinkish and slightly white variegated foliage, is disclosed.

3 Drawing Sheets

Genus and species: *Weigela florida*.
Variety denomination: 'Verweig 4'.

BACKGROUND OF THE INVENTION

The present invention comprises a new and distinct cultivar of *Weigela*, botanically known as *Weigela florida*, and hereinafter referred to by the cultivar name 'Verweig 4'. This new Weigela was discovered as a naturally-occurring branch mutation from the *Weigela* plant 'Verweig' (U.S. Plant Pat. No. 16,824) in summer 2007 in Hazerswoude, The Netherlands in a cultivated area (outdoor nursery). 'Verweig 4' has been asexually reproduced repeatedly by softwood cuttings in Hazerswoude, The Netherlands for over two generations.

'Verweig 4' has been found to retain its distinctive characteristics through successive asexual propagations.

Plant Breeder's Rights for this cultivar have been applied for in the European Union in May 2009. 'Verweig 4' has not been made publicly available or sold more than one year prior to the filing date of this application.

SUMMARY OF THE INVENTION

The following are the most outstanding and distinguishing characteristics of this new cultivar when grown under normal horticultural in Hazerswoude, The Netherlands.

1. Purple flowers;
2. A moderately vigorous growth habit; and
3. Green, pinkish and slightly white variegated foliage.

DESCRIPTION OF THE PHOTOGRAPHS

This new *Weigela* plant is illustrated by the accompanying photographs which show the plant's form, foliage and flowers. The colors shown are as true as can be reasonably obtained by conventional photographic procedures. The photographs were taken in May 2009 on two year-old plants, growing in three-liter pots.

DESCRIPTION OF THE NEW CULTIVAR

Figure 1:
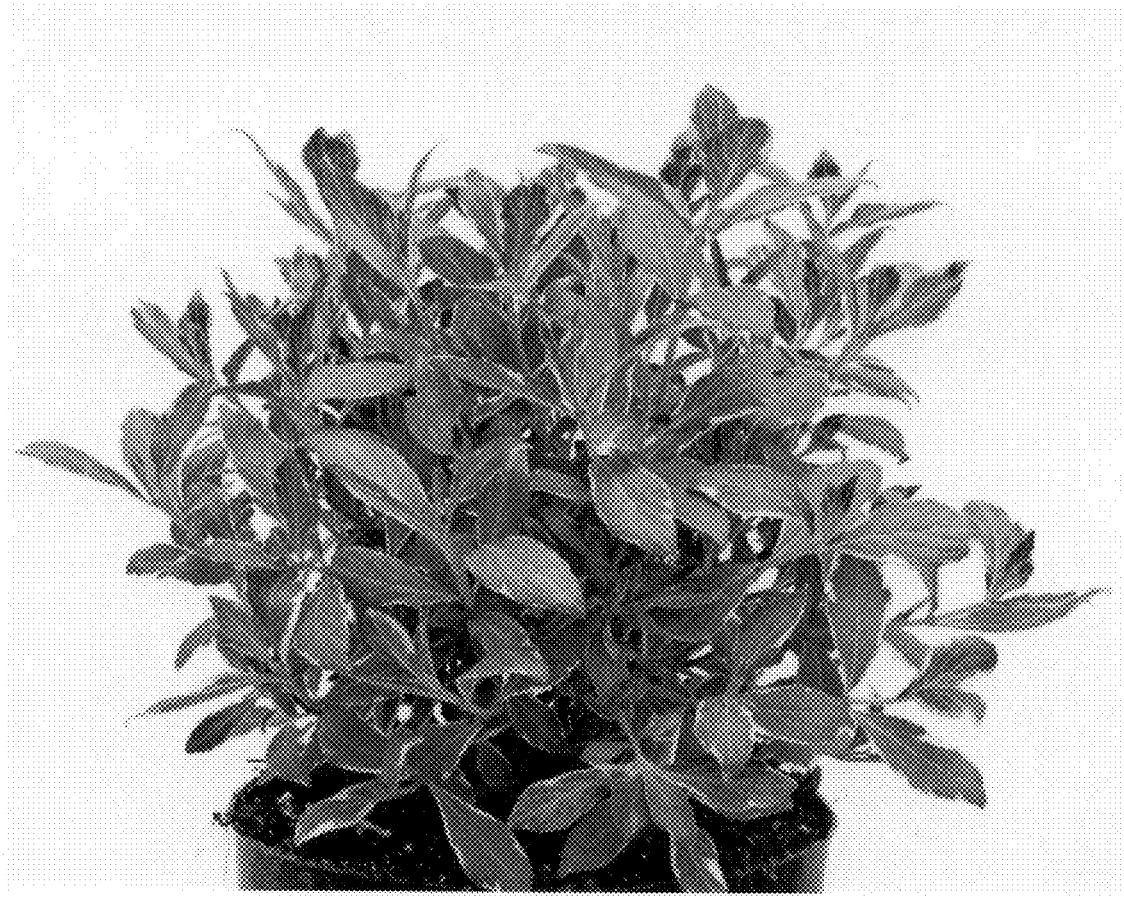
FIG. 1 shows a photo of the whole plant, including foliage.
Figure 2:
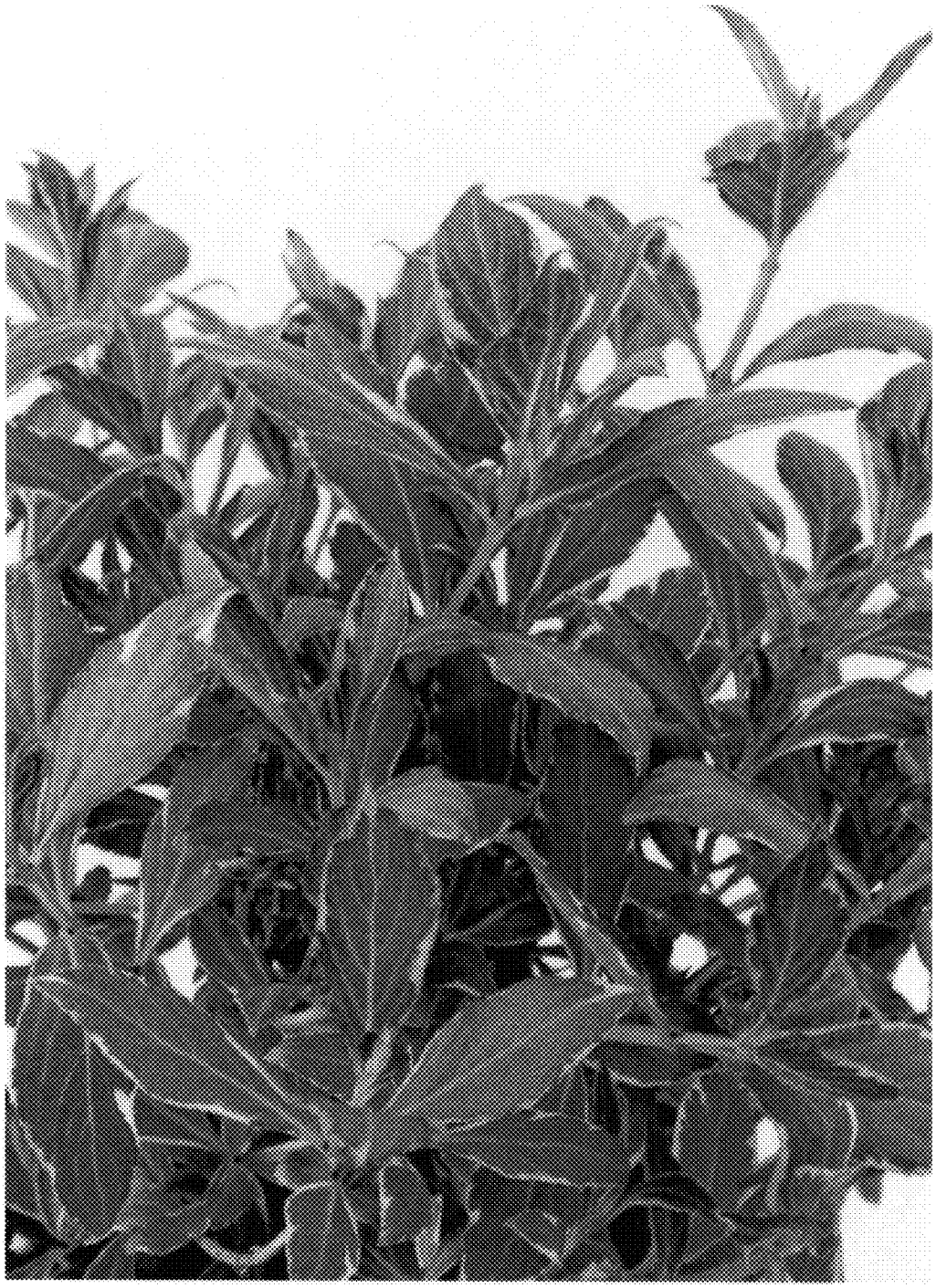
FIG. 2 shows a close-up photo of the foliage.
Figure 3:
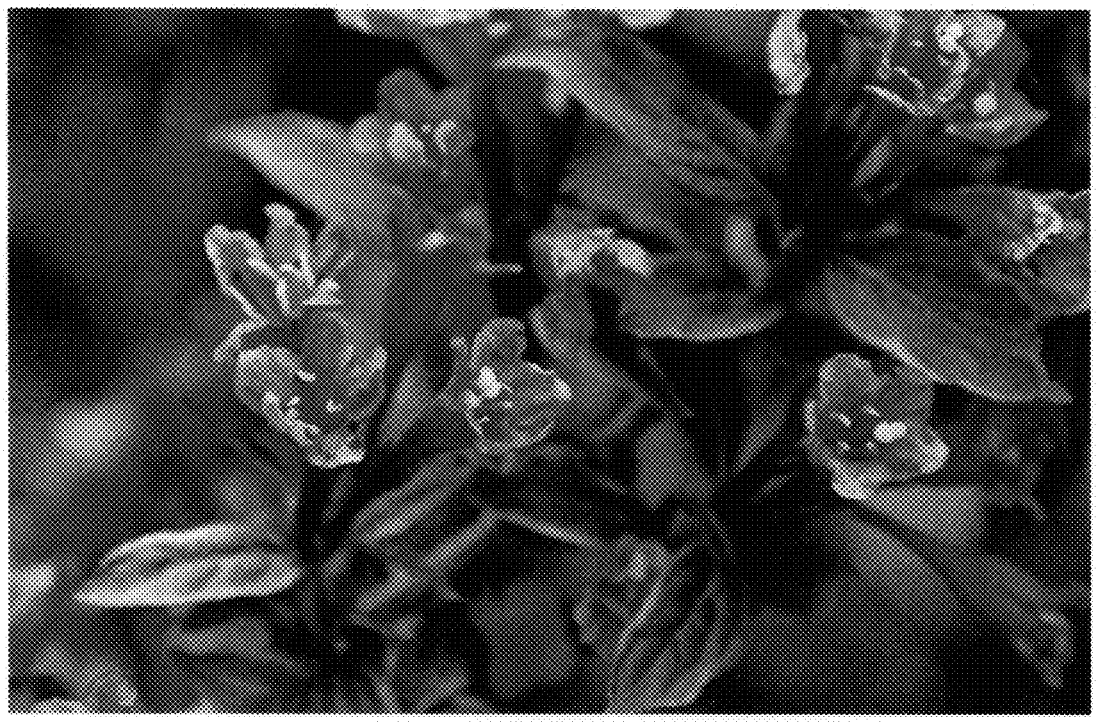
FIG. 3 shows a close-up of the flowers.

The following detailed description sets forth the distinctive characteristics of 'Verweig 4'. The detailed description was taken from two year-old plants in May 2009 and growing outdoors in three-liter pots under natural light. The plants were not pinched. Color references are to The R.H.S. Colour Chart of The Royal Horticultural Society of London (R.H.S.), 2007 5$^{th}$ Edition.

DETAILED BOTANICAL DESCRIPTION

Classification:

*Botanical name.*—*Weigela florida.*

*Denomination.*—'Verweig 4'.

Parentage: Naturally-occurring branch mutation from parent 'Verweig' (U.S. Plant Pat. No. 16,824).

Growing conditions:

*Range of day temperatures.*—12° C. to 23° C.

*Range of night temperatures.*—4° C. to 14° C.

*Photoperiodic treatments.*—None.

*Growth retardants.*—None.

Plant:

*Type.*—Perennial, shrub.

*Growth habit.*—Moderately vigorous, broad-upright and freely branching.

*Growth rate.*—Approximately 5.0 cm per month in the spring.

*Plant shape.*—Irregular-globular.

*Height at maturity.*—23.2 cm.

*Width at maturity.*—34.6 cm.

*High temperature tolerance.*—At least tolerant up to 35° C., USDA Zone 9.

*Low temperature tolerance.*—At least hardy up to USDA Zone 5.

*Number of days to initiate roots.*—21 to 28 days in the summer in an average temperature of 18° C.

*Time to produce a rooted liner.*—Approximately 60 days in the summer in average temperatures between 16° C. to 22° C.

*Root description.*—Moderately dense root production; roots are light-brown; main roots are moderately thick while other roots are moderately fine; are moderately free-branching.

Branches:

*Branching habit.*—Free-branching with basal branching; pinching is not required but it will improve the branching.

*Quantity of lateral branches per plant.*—Average is 45.

*Appearance and shape.*—Rounded, moderately glossy.

*Aspect.*—Upright to outward in an average angle of 20° (but ranges from angles of 0° to 45°).

*Strength.*—Moderate.

*Lateral branch length.*—Average is 10.0 cm.

*Lateral branch diameter: Average is* 0.2 cm.

*Internode length.*—3.2 cm.

*Color.*—RHS 144B (Yellow-green); older branches and bark become RHS 199B and RHS 199C (Greyed-brown) with maturity.

*Texture.*—The upper internodes of the immature stems (shoots) are covered with moderately dense, soft short pubescence that is RHS 157D (Green-white) and approximately 0.1 cm in length.

Leaves:

*Arrangement.*—Opposite and single.

*Quantity of leaves per lateral branch.*—Average is 8.

*Durability of foliage to stresses.*—High.

*Shape.*—Narrow elliptic to narrow obovate.

*Apex.*—Acuminate.

*Base.*—Attenuate.

*Margin.*—Finely serrate.

*Length.*—Average is 4.8 cm.

*Width.*—Average is 2.1 cm.

*Texture.*—Moderately glossy on both surfaces; the margins, the upper surface main vein and the lower surface of the secondary veins are moderately covered with RHS 157D (Green-white) pubescence that are 0.05 cm in length.

*Color, immature leaves.*—Upper surface: RHS 147A (Yellow-green), RHS N137A and RHS N137B (Green) towards the base and RHS 181C and RHS 181D (Greyed-red) on the margins. Lower surface: Between RHS 147A (Yellow-green) and RHS 197A (Greyed-green) and RHS 182C (Greyed-red) on the margins.

*Color, mature leaves.*—Upper surface: RHS 137B (Green) and the margins are RHS N155D (White) and RHS 181C and RHS 181D (Greyed-red). Lower surface: RHS 147B (Yellow-green) and the margins are RHS N155D (White) and RHS 181C (Greyed-red).

*Venation.*—Pattern: Pinnate. Color, upper surface: RHS 144C (Yellow-green). Color, lower surface: RHS 145C and RHS 145D (Yellow-green).

*Petiole.*—Length: Average is 0.3 cm. Diameter: Average is 0.15 cm. Color: RHS 144C (Yellow-green). Texture: Not pubescent.

Bud:

*Quantity of flower buds per lateral stem.*—Average is 14.

*Shape.*—Narrow obovate.

*Rate of opening.*—Approximately 2 days.

*Length.*—2.7 cm.

*Diameter.*—0.6 cm

*Color.*—Between RHS 59B (Red-purple) and RHS 187C (Greyed-purple); base is slightly darker and between RHS 59A and RHS 187B.

Flower:

*Arrangement and type.*—Solitary and in pairs, terminal and in leaf axils; self-cleaning.

*Form.*—Single and trumpet-shaped.

*Aspect.*—Outward and upright.

*Flowering habit.*—Flowers once per year during in the spring (May).

*Quantity of flowers per lateral stem.*—Average is 14.

*Quantity of flowers and buds per plant.*—Average is 600.

*Time to produce a finished flowering plant.*—Approximately 11 months.

*Rate of flower opening.*—Approximately 90% of the flowers are open at a given time.

*Lastingness of flowers on the plant.*—Approximately 12 days.

*Fragrance.*—Absent.

*Height* (*depth*).—Average is 3.0 cm.

*Diameter.*—Average is 1.5 cm.

*Petals.*—Appearance: Slightly glossy, the lower ¾ of the petals are fused at the base. Arrangement: Rotate and fused into a trumpet-shaped corolla. Shape: Spathulate. Apex: Obtuse. Base: Fused. Margin: Entire for upper ¼ of petal. Quantity per flower: Average is 5. Length: Average is 3.0 cm. Width: Approximately 0.7 cm (the upper ¼ or free part of the petal). Texture: The lower surface is densely covered with very short RHS N155B and RHS N155C (White) pubescence that are approximately 0.01 cm in length and the upper surface is smooth (not pubescent). Color, when opening: The upper surface is between RHS 64A (Red-purple) and RHS N77B (Purple) and the lower surface is RHS 59B and RHS 59C (Red-purple). Color, fully opened: The upper surface is between RHS 64A (Red-purple) and RHS N77B (Purple) and the lower surface is RHS 59B and RHS 59C (Red-purple). Color fading to: Petal color does not fade.

*Pedicel.*—Length: 0.9 cm. Diameter: 0.15 cm. Angle: Average is 5°. Strength: Moderately strong. Color: RHS 200A (Brown).

Calyx:

*Shape and arrangement.*—Composed of 5 sepals in a rotate arrangement

*Calyx.*—Length: Average is 0.8 cm. Diameter: Average is 0.7 cm.

*Sepal.*—Appearance (both upper and lower surfaces): Slightly glossy and smooth. Shape: Linear. Apex: Narrow acute. Base: Narrow cuneate. Margin: Entire. Length: Average is 0.9 cm. Width: Average is 0.1 cm. Color, immature and mature (both upper and lower surfaces): RHS 146D (Yellow-green) and heavily spotted with RHS N186C (Greyed-purple).

Reproductive organs:

*Stamen.*—Quantity per flower: 5. Filament length: 2.4 cm. Filament color: RHS 65B (Red-purple). Anther: Length: 0.3 cm. Shape: Basifixed, narrow-oblong. Color: RHS 158C and RHS 158D (Yellow-white). Pollen color: RHS 158D (Yellow-white). Pollen amount: Sparse.

*Pistil.*—Quantity: 1. Length: Average is 2.7 cm.

*Stigma.*—Shape: Club-shaped. Color: RHS 155A (White).

*Style.*—Length: 2.5 cm. Color: RHS 155A.

*Ovary color.*—RHS 200A (Brown).

Fruit/seed set: No fruit or seed set has been observed.

Disease and insect resistance: Typical of *Weigela florida* species.

Outdoor performance: Good rain and wind tolerance.

COMPARISON WITH PARENTAL LINE AND KNOWN CULTIVAR

'Verweig 4' is distinguished from the parent 'Verweig' (U.S. Plant Pat. No. 16,824) in that 'Verweig 4' has a more vigorous growth habit and has less white variegation of the leaves than 'Verweig'. Additionally, 'Verweig 4' has smaller leaves (length 4.8 cm and width is 2.1 cm) than 'Verweig' (length is 7.3 cm and width is 3.0 cm).

Verweig 4' is distinguished from the commercial comparison variety 'Carlton' (U.S. Plant Pat. No. 20,025) in that Verweig 4' is smaller (23.3 cm in height and 34.6 cm in width) than 'Carlton' (2 meters in height and 1.7 meters in diameter). Additionally, 'Verweig 4' has smaller leaves (length 4.8 cm and width is 2.1 cm) than 'Carlton' (length is 10.0 cm and width is 5.0 cm).

I claim:

1. A new and distinct cultivar of *Weigela* plant as shown and described herein.

* * * * *